US006918981B2

(12) United States Patent
Ko et al.

(10) Patent No.: US 6,918,981 B2
(45) Date of Patent: *Jul. 19, 2005

(54) PROCESS FOR ADDING SUPERABSORBENT TO A PRE-FORMED FIBROUS WEB USING TWO POLYMER PRECURSOR STREAMS

(75) Inventors: Young C. Ko, Neenah, WI (US); Stanley R. Kellenberger, Appleton, WI (US); David Martin Jackson, Roswell, GA (US); Dave A. Soerens, Neenah, WI (US); Jason M. Laumer, Appleton, WI (US); Sridhar Ranganathan, Suwanee, GA (US); Richard Harry Thiessen, Appleton, WI (US); Varunesh Sharma, Atlanta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 248 days.

This patent is subject to a terminal disclaimer.

(21) Appl. No.: 10/017,760

(22) Filed: Dec. 14, 2001

(65) Prior Publication Data

US 2003/0111163 A1 Jun. 19, 2003

(51) Int. Cl.[7] .................................................. B05D 1/36
(52) U.S. Cl. ...................... 156/181; 156/277; 156/279; 427/337; 427/392; 427/393; 427/407.1; 264/109; 264/122
(58) Field of Search ........................... 156/62.2, 180, 156/181, 277, 279; 427/392, 393, 331, 337, 407.1; 264/109, 122

(56) References Cited

U.S. PATENT DOCUMENTS

| 3,338,992 A | 8/1967 | Kinney |
| 3,341,394 A | 9/1967 | Kinney |
| 3,502,538 A | 3/1970 | Petersen |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 3,901,236 A | 8/1975 | Assarsson et al. |
| 4,076,663 A | 2/1978 | Masuda et al. |
| 4,100,324 A | 7/1978 | Anderson et al. |
| 4,151,130 A | 4/1979 | Adams ................ 260/17.4 GC |
| 4,286,082 A | 8/1981 | Tsubakimoto et al. |
| 4,340,563 A | 7/1982 | Appel et al. |
| 4,500,315 A | 2/1985 | Pieniak et al. |
| 4,537,590 A | 8/1985 | Pieniak et al. |
| 4,540,454 A | 9/1985 | Pieniak et al. |
| 4,559,050 A | 12/1985 | Iskra |
| 4,560,372 A | 12/1985 | Pieniak |
| 4,596,567 A | 6/1986 | Iskra |
| 4,605,402 A | 8/1986 | Iskra |
| 4,676,784 A | 6/1987 | Erdman et al. |
| 4,699,823 A | 10/1987 | Kellenberger et al. |
| 4,818,464 A | 4/1989 | Lau |
| 4,888,238 A | 12/1989 | Katz et al. ................ 428/378 |
| 4,892,754 A | * 1/1990 | Itoh et al. ................ 427/513 |
| 4,902,559 A | 2/1990 | Eschwey et al. |
| 4,958,385 A | 9/1990 | Rushton, Jr. ................ 2/174 |
| 5,059,664 A | 10/1991 | Yada et al. ................ 526/240 |
| 5,071,681 A | 12/1991 | Manning et al. ............ 427/392 |
| 5,175,046 A | 12/1992 | Nguyen ................ 428/198 |
| 5,248,524 A | 9/1993 | Soderlund ................ 427/200 |
| 5,298,284 A | 3/1994 | Buckwald et al. .......... 427/203 |
| 5,300,565 A | 4/1994 | Berg et al. ................ 525/54.2 |
| 5,350,624 A | 9/1994 | Georger et al. |
| 5,422,169 A | 6/1995 | Roe |
| 5,454,801 A | 10/1995 | Lauritzen ................ 604/378 |
| 5,487,736 A | 1/1996 | Van Phan ................ 604/368 |
| 5,489,469 A | 2/1996 | Kobayashi et al. ......... 428/283 |

(Continued)

FOREIGN PATENT DOCUMENTS

| DE | 199 05 947 A1 | 8/2000 | ......... A61L/15/60 |
| EP | 0 022 792 B1 | 5/1984 | ......... A61F/13/16 |
| EP | 0 290 814 A2 | 11/1988 | ......... C08F/20/06 |
| EP | 0 301 804 A2 | 2/1989 | ......... D04H/1/00 |
| EP | 0 301 804 A3 | 5/1990 | ......... D04H/1/56 |
| EP | 0 390 513 A2 | 10/1990 | ......... A61L/15/00 |
| EP | 0 402 650 A2 | 12/1990 | ......... A61L/15/22 |
| EP | 0 390 513 A3 | 8/1991 | ......... A61L/15/00 |
| EP | 0 402 650 A3 | 11/1991 | ......... A61L/15/22 |
| EP | 0 223 908 B1 | 2/1993 | ......... D04H/1/64 |
| EP | 719 531 | 7/1996 | |
| EP | 729 336 | 6/1998 | |
| EP | 0 729 336 B1 | 6/1998 | ......... A61F/13/46 |
| EP | 0 992 250 A2 | 4/2000 | ......... A61F/15/60 |
| EP | 1 142 696 A1 | 10/2001 | |
| EP | 1 178 149 A1 | 2/2002 | |
| WO | WO 95/13777 | 5/1995 | ......... A61F/13/46 |
| WO | 95/13778 | 5/1995 | |
| WO | WO 95/13778 | 5/1995 | ......... A61F/13/46 |
| WO | WO 96/23024 | 8/1996 | |
| WO | 98/51251 | 11/1998 | |
| WO | WO 99/34041 | 7/1999 | ......... D01F/6/36 |
| WO | 00/55418 | 9/2000 | |
| WO | 01/23177 | 4/2001 | |
| WO | WO 01/31123 A1 | 5/2001 | ......... D21H/21/20 |
| WO | WO 01/56625 A2 | 8/2001 | ......... A61L/15/00 |
| WO | WO 01/56625 A3 | 8/2001 | ......... A61L/15/00 |
| WO | WO 02/053363 A2 | 7/2002 | ......... B23B/3/08 |
| WO | WO 03/051253 A1 | 6/2003 | |
| WO | WO 03/051945 A1 | 6/2003 | |

OTHER PUBLICATIONS

English Translation of Abstract and Claims 1–10 of JP 11–93073A, Kao Corporation (2 pages).

*Primary Examiner*—Sam Chuan Yao
(74) *Attorney, Agent, or Firm*—Pauley Petersen & Erickson

(57) ABSTRACT

A process for making an absorbent fibrous web composite including a stable, controllable dispersion of superabsorbent polymer is provided. A pre-formed web, desirably including cellulose fibers and, optionally, thermoplastic fibers is provided. First and second superabsorbent polymer precursor compositions are added to the fibrous web using separate streams. The first and second superabsorbent polymer precursor compositions combine with each other and chemically react on or in the fibrous web, to form a superabsorbent polymer which sticks to the surface of the fibrous web.

27 Claims, No Drawings

U.S. PATENT DOCUMENTS

| | | | |
|---|---|---|---|
| 5,506,035 A | 4/1996 | Van Phan et al. | 428/196 |
| 5,547,747 A * | 8/1996 | Trokhan et al. | 428/320.2 |
| 5,549,928 A | 8/1996 | Trokhan et al. | |
| 5,620,742 A | 4/1997 | Lauritzen | 427/209 |
| 5,674,478 A | 10/1997 | Dodd et al. | |
| 5,817,081 A | 10/1998 | LaVon et al. | |
| 5,821,179 A | 10/1998 | Masaki et al. | |
| 5,868,724 A | 2/1999 | Dierckes, Jr. et al. | 604/368 |
| 5,875,967 A | 3/1999 | Ruth, III | |
| 5,962,068 A | 10/1999 | Tsuchiya et al. | |
| 5,998,312 A | 12/1999 | Kroesbergen | 442/221 |
| 6,019,457 A | 2/2000 | Silverbrook | |
| 6,022,610 A | 2/2000 | Phan et al. | |
| 6,024,438 A | 2/2000 | Koike et al. | |
| 6,043,311 A | 3/2000 | Houben et al. | 524/522 |
| 6,086,950 A | 7/2000 | Masaki et al. | |
| 6,103,061 A * | 8/2000 | Anderson et al. | 162/108 |
| 6,235,659 B1 | 5/2001 | McAmish et al. | 442/79 |
| 6,242,073 B1 | 6/2001 | Phan et al. | 428/132 |
| 6,417,425 B1 * | 7/2002 | Whitmore et al. | 604/367 |
| 6,533,989 B1 * | 3/2003 | Wisneski et al. | 264/510 |
| 2003/0149413 A1 | 8/2003 | Mechawej | 604/368 |
| 2003/0205318 A1 | 11/2003 | Ko et al. | |
| 2003/0211248 A1 | 11/2003 | Ko et al. | |

* cited by examiner

US 6,918,981 B2

PROCESS FOR ADDING SUPERABSORBENT TO A PRE-FORMED FIBROUS WEB USING TWO POLYMER PRECURSOR STREAMS

FIELD OF THE INVENTION

This invention relates to a process for making absorbent material useful in personal care absorbent articles, medical absorbent articles and the like, in which a superabsorbent polymer component of the absorbent material is formed by separately adding two or more polymer precursor compositions to the nonwoven web. The polymer precursor compositions react in or on the nonwoven web upon contacting each other, causing in situ formation of the superabsorbent polymer.

BACKGROUND OF THE INVENTION

Processes for making absorbent composite materials having a superabsorbent polymer component are known. In various processes, preformed superabsorbent polymer particles or fibers are combined with cellulose fibers, thermoplastic fibers and the like in a web formation process to make a composite web structure. Illustrative processes are disclosed in U.S. Pat. No. 4,818,464 to Lau, U.S. Pat. No. 4,100,324 to Anderson et al., U.S. Pat. No. 5,350,624 to Georger et al., and U.S. Pat. No. 4,902,559 to Eschwey et al. These processes are commonly referred to as "coform" processes.

Additionally, a process is known where a superabsorbent polymer is only partially formed from a precursor monomer before being added to a fibrous substrate, and the polymerization is completed after the partially polymerized monomer contacts the substrate. U.S. Pat. No. 5,962,068 to Tsuchiya et al. discloses a water-absorptive composite including a fibrous substrate and water-absorptive polymer particles. The water-absorptive polymer is partially polymerized with the aid of a redox initiator before being added to the fibrous substrate. The partially polymerized material is added in a dropwise fashion in a single stream to the substrate, and the polymerization reaction then proceeds to completion.

One feature that the known processes have in common, is that they require at least some separate process steps for polymerizing or partially polymerizing the superabsorbent material before it can be added to the fibrous substrate. In other words, neither process totally forms the superabsorbent polymer within the fibrous substrate.

DEFINITIONS

The term "cellulose fibers" refers to fibers from natural sources such as woody and non-woody plants, regenerated cellulose, and the derivatives from these fibers by means of chemical, mechanical, thermal treatment, or any combination of these. Woody plants include, for example, deciduous and coniferous trees. Non-woody plants include, for instance, cotton, flax, esparto grass, milkweed, straw, jute hemp, and bagasse. Regenerated cellulose fibers include, for instance, viscose and rayon. The cellulose derivatives include, for instance, microcrystalline cellulose, chemically crosslinked fibers, and un-crosslinked, twisted fibers.

The term "average fiber length" refers to a weighted average length of fiber determined using a Kajaani fiber analyzer Model No. FS-100 available from Kajaani Oy Electronics in Kajaani, Finland. Under the test procedure, a fiber sample is treated with a macerating liquid to ensure that no fiber bundles or shives are present. Each fiber sample is dispersed in hot water and diluted to about a 0.001% concentration. Individual test samples are drawn in approximately 50 to 500 ml portions from the dilute solution and tested using the standard Kajaani fiber analysis procedure. The weighted average fiber lengths may be expressed by the following equation:

$$\sum_{X_i>0}^{k} (X_1 * n_1)/n$$

where k=maximum fiber length,
  $X_i$=individual fiber length,
  $n_1$=number of fibers having length $X_i$
and
  n=total number of fibers measured.

The term "meltblown fibers" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than 10 microns in diameter, and are generally self bonding when deposited onto a collecting surface.

The term "spunbonded fibers" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, U.S. Pat. No. 3,502,538 to Petersen, and U.S. Pat. No. 3,542,615 to Dobo et al. Spunbond fibers are quenched and generally not tacky on the surface when they enter the draw unit, or when they are deposited onto a collecting surface. Spunbond fibers are generally continuous and may have average diameters larger than 7 microns, often between about 10 and 30 microns.

The term "staple filaments or fibers" means filaments or fibers which are natural or which are cut from a manufactured filament prior to forming into a web, and which have a length ranging from about 0.1–15 cm, more commonly about 0.2–7 cm.

The term "microfibers" means small diameter fibers having an average diameter not greater than about 75 microns, for example, having an average diameter of from about 1 micron to about 50 microns, or more particularly, having an average diameter of from about 1 micron to about 30 microns.

The term "substantially continuous filaments or fibers" refers to filaments or fibers prepared by extrusion from a spinnerette, including without limitation spunbonded and meltblown fibers, which are not cut from their original length prior to being formed into a fibrous web. Substantially continuous filaments or fibers may have lengths ranging from greater than about 15 cm to more than one meter; and up to the length of the nonwoven web or fabric being formed. The definition of "substantially continuous filaments or fibers" includes those which are not cut prior to being formed into a fibrous web, but which are later cut when the nonwoven web or fabric is cut.

The term "nonwoven web" means a web having a structure of individual fibers or filaments which are interlaid, but not in an identifiable manner as in a knitted fabric. "Fibrous" webs include nonwoven webs as well as webs where the fibers are interlaid in an identifiable (e.g., regular) manner. The terms "fiber" and "filament" are used herein interchangeably. Nonwoven webs have been formed from many processes such as, for example, meltblowing processes, spunbonding processes, air laying processes, and bonded carded web processes. The term also includes films that have been perforated or otherwise treated to allow air to pass through. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91.)

The term "polymer" generally includes but is not limited to, homopolymers, copolymers, including block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

The term "wettable" and/or "hydrophilic" is meant to refer to a fiber which exhibits a liquid such as water, synthetic urine, or a 0.9 weight percent aqueous saline solution, in air contact angle of less than 90°. The contact angle may be determined, for example, in accordance with ASTM D724-89.

The term "thermoplastic" is meant to describe a material that softens and flows when exposed to heat and which substantially returns to its original hardened condition when cooled to room temperature.

The term "superabsorbent polymer precursor composition" refers to any and all solutions which, when mixed, chemically react to form a superabsorbent polymer. Each solution may be comprised of any combination of oligomer(s), monomer(s), crosslinking reagent(s), neutralizing agent, or initiator(s). In instances when only a single solution is utilized all the desired components must be in said solution and the initiator(s) must require a later activation step (e.g., heating or irradiation). In instances when two or more solutions are utilized the initiator(s) is most often, but not limited to, a chemical redox pair. When a redox pair, comprised of an oxidizing radical generator and a reducing agent, is used as the initiator the oxidizing radical generator and reducing agent must be in separate solutions. The solution of oxidizing radical generator or reducing agent may also contain any combination of oligomer(s), monomers(s), crosslinking reagent(s), or neutralizing agent.

The terms "elastic" and "elastomeric" are used interchangeably to mean a material that is generally capable of recovering its shape after deformation when the deforming force is removed. Specifically, as used herein, elastic or elastomeric is meant to be that property of any material which upon application of a biasing force, permits that material to be stretchable to a stretched biased length which is at least about 50 percent greater than its relaxed unbiased length, and that will cause the material to recover at least 40 percent of its elongation upon release of the stretching elongating force. A hypothetical example which would satisfy this definition of an elastomeric material would be a one (1) inch sample of a material which is elongatable to at least 1.50 inches and which, upon being elongated to 1.50 inches and released, will recover to a length of not more than 1.30 inches. Many elastic materials may be stretched by much more than 50 percent of their relaxed length, and many of these will recover to substantially their original relaxed length upon release of the stretching, elongating force.

The term "recover" or "retract" relates to a contraction of a stretched material upon termination of a biasing force following stretching of the material by application of the biasing force.

The term "superabsorbent material" refers to a water swellable, water-insoluble organic or inorganic material capable, under the most favorable conditions, of absorbing at least about 15 times its weight, preferably at least about 20 times its weight in an aqueous solution containing 0.9% by weight sodium chloride. The term "absorbent material" refers to any material capable of absorbing from about 5 to less than about 15 times its weight of the same solution.

The term "personal care absorbent article" includes diapers, training pants, swim wear, absorbent underpants, adult incontinence products, feminine hygiene products, and the like.

The term "medical absorbent article" includes medical absorbent garments, drapes, gowns, bandages, wound dressings, underpads, wipes, and the like.

The term "tissue and towel article" includes facial and bathroom tissue, paper towels, wet wipes, and the like.

SUMMARY OF THE INVENTION

The present invention is directed to a process for making an absorbent fibrous web composite in which a fibrous web is initially formed from absorbent and/or other hydrophilic fibers and, optionally, thermoplastic fibers. Then, a superabsorbent polymer is completely formed in situ in the fibrous web by separately adding two or more superabsorbent polymer precursor compositions to the fibrous web. The two or more superabsorbent polymer precursor compositions chemically react upon contacting each other, to form a superabsorbent polymer. Alternatively, each precursor composition may contain a corresponding component of a chemical redox pair (an oxidizing radical generator and a reducing agent) and, in addition, one or both precursor compositions may include any combination of oligomer(s), monomer(s), crosslinking reagent(s) and/or neutralizing agent(s). Because the superabsorbent polymer precursor compositions initially contact each other during or after making contact with the fibrous web, the entire polymerization reaction proceeds on or in the fibrous web.

The superabsorbent polymer precursor compositions are separately added to the fibrous web using any suitable technique or techniques. Suitable addition processes include contact printing, embossing, non-contact printing, dropwise addition, spraying, dipping and the like. The two or more superabsorbent polymer precursor compositions are added separately, meaning that they are not mixed together or otherwise in contact with each other before being added to the fibrous web. The precursor compositions are selected so that the polymerization reaction for making superabsorbent proceeds entirely on or in the fibrous web, when the precursor compositions are in contact with each other.

As a result, the superabsorbent polymer(s) are formed directly onto the surface of fibers. The resulting absorbent fibrous web composite has a controlled, stable composition in which the superabsorbent polymer sticks to the fibers and does not migrate within or away from the absorbent nonwoven web composite.

Additional surface crosslinking may also be performed on the superabsorbent material once the initial polymerization has taken place. The surface crosslinking may enhance the absorbent properties of the material.

DETAILED DESCRIPTION OF THE PRESENTLY PREFERRED EMBODIMENTS

In accordance with the invention, a pre-formed web of fibers is provided. The web may be a nonwoven web, for instance, and contains about 25–100% by weight of absorbent and/or other hydrophilic fibers and about 0–75% by weight of thermoplastic fibers, suitably about 50–100% by weight absorbent and/or other hydrophilic fibers and about 0–50% by weight thermoplastic fibers, desirably about 60–90% by weight absorbent and/or other hydrophilic fibers and about 10–40% by weight thermoplastic fibers. The starting fibrous web may be formed using any conventional technique.

Desirably, the hydrophilic fibers include cellulose fibers. Examples of cellulose fibers include without limitation wood pulp fibers, wood pulp fluff, curled pulp fibers, microcrystalline cellulose, microfibrallar cellulose, cotton, and the like. Other hydrophilic fibers may also be employed, as well as absorbent staple fibers. Pre-formed superabsorbent particles or fibers may also be included. However, for purposes of the invention, at least some superabsorbent polymer must be formed in situ as described below.

When thermoplastic fibers are employed, they may include meltblown fibers. The meltblown fibers may be formed from thermoplastic polymers including, without limitation, polyolefins, polyamides, polyester, polyurethane, polyvinyl alcohol, polycaprotactone, styrene butadiene block copolymers or the like. Suitable polyolefins include without limitation polyethylene, polypropylene, polybutylene, copolymers of ethylene with other alpha-olefins, copolymers of propylene with other alpha-olefins, copolymers of butylene with other alpha-olefins, and combinations thereof. Processes for forming absorbent nonwoven webs containing hydrophilic fibers, meltblown fibers, and other optional ingredients are disclosed in U.S. Pat. No. 5,350,624 to Georger et al.; U.S. Pat. No. 4,818,464 to Lau; and U.S. Pat. No. 4,100,324 to Anderson et al.; the disclosures of which are incorporated by reference.

When thermoplastic polymers are employed, they may include spunbond fibers formed from any of the thermoplastic polymers listed above as being useful for meltblown fibers. A process for forming absorbent nonwoven webs containing hydrophilic fibers, spunbond fibers, and other optional ingredients is disclosed in U.S. Pat. No. 4,902,559 to Eschwey et al., the disclosure of which is incorporated by reference.

In accordance with the invention, two or more superabsorbent polymer precursor compositions are separately applied to the fibrous web. By "separately applied" it is meant that the two precursor compostions are applied in a manner where they do not contact each other before they contact the fibrous web. Also, the superabsorbent polymer precursor compositions are selected so that they do not polymerize or otherwise chemically react before they make contact with each other. The precursor compositions initially contact each other upon or after being applied to the fibrous web. Desirably, the superabsorbent polymer precursor compositions are selected so that they spontaneously react, i.e., begin polymerizing, immediately after they contact each other. However, the superabsorbent polymer precursor compositions may alternatively be designed so that they chemically react after being combined, only after an activation step is performed. Depending on the specific chemical reaction(s), such activation may require heating the fibrous web to a predetermined temperature, irradiating the fibrous web (e.g., using ultraviolet radiation), agitation, compression, or some other technique.

The superabsorbent polymer precursor compositions may be applied to the fibrous web using a wide variety of different processes. Suitable processes include spraying, where the two precursor compositions are sprayed using different nozzles and/or at different times; contact printing or embossing, using separate printing or embossing steps; non-contact printing, using separate printing nozzles and/or steps; dipping, where the fibrous web is first dipped into a solution containing the first precursor composition and later dipped into a solution containing the second precursor composition; and the like. Suitable non-contact printing processes for applying the superabsorbent polymer precursor compositions are disclosed in U.S. Pat. No. 6,024,438 to Koike et al.; U.S. Pat. No. 6,019,457 to Silverbrook; and U.S. Pat. No. 5,875,967 to Ruth III; which are incorporated by reference. Desirably, the superabsorbent polymer precursor compositions are applied as droplets or microdroplets, having a diameter of about 10–1000 microns, desirably about 50–500 microns. The microdroplets may have a viscosity of about 5–1000 centipoise, suitably about 10–500 centipoise, desirably about 20–100 centipoise at the application temperature (typically room temperature).

A wide variety of superabsorbent polymer precursor compositions may be employed in the process of the invention. At least one polymer precursor composition may include a monomer. Suitable superabsorbent-forming monomers include the following monomer, and combinations thereof:

1. Carboxyl group-containing monomers: monoethylenically unsaturated mono or poly-carboxylic acids, such as (meth)acrylic acid (meaning acrylic acid or methacrylic acid. Similar notations are used hereinafter), maleic acid, fumaric acid, crotonic acid, sorbic acid, itaconic acid, and cinnamic acid;

2. Carboxylic acid anhydride group-containing monomers: monoethylenically unsaturated polycarboxylic acid anhydrides (such as maleic anhydride);

3. Carboxylic acid salt-containing monomers: water-soluble salts (alkali metal salts, ammonium salts, amine salts, etc.) of monoethylenically unsaturated mono- or poly-carboxylic acids (such as sodium (meth)acrylate, trimethylamine (meth)acrylate, triethanolamine (meth)acrylate, sodium maleate, methylamine maleatel;

4. Sulfonic acid group-containing monomers: aliphatic or aromatic vinyl sulfonic acids (such as vinylsulfonic acid, allyl sulfonic acid, vinyltoluenesulfonic acid, stryrene sulfonic acid), (meth)acrylic sulfonic acids [such as sulfopropyl (meth)acrylate, 2-hydroxy-3-(meth)acryloxy propyl sulfonic acid];

5. Sulfonic acid salt group-containing monomers: alkali metal salts, ammonium salts, amine salts of sulfonic acid group containing monomers as mentioned above;

6. Hydroxyl group-containing monomers: monoethylenically unsaturated alcohols [such as (meth)allyl alcohol], monoethylenically unsaturated ethers or esters of polyols (alkylene glycols, glycerol, polyoxyalkylene polyols), such as hydroxethyl (meth)acrylate, hydroxypropyl (meth)acrylate, triethylene glycol (meth)acrylate, poly (oxyethylene oxypropylene) glycol mono (meth)allyl ether (in which hydroxyl groups may be etherified or esterified);

7. Amide group-containing monomers: vinylformamide, (meth)acrylamide, N-alkyl (meth)acrylamides (such as N-methylacrylamide, N-hexylacrylamide), N,N-dialkyl (meth)acryl amides (such as N,N-dimethylacrylamide, N,N-di-n-propylacrylamide), N-hydroxyalkyl (meth)acrylamides [such as N-methylol (meth)acrylamide, N-hydroxyethyl (meth)acrylamidel, N,N-dihydroxyalkyl (meth)acrylamides [such as N,N-dihydroxyethyl (meth)acrylamidel, vinyl lactams (such as N-vinylpyrrolidone);

8. Amino group-containing monomers: amino group-containing esters (e.g., dialkylaminoalkyl esters, dihydroxyalkylaminoalkyl esters, morpholinoalkyl esters, etc.) of monoethylenically unsaturated mono-or di-carboxylic acid [such as dimethlaminoethyl (meth)acrylate, diethylaminoethyl (meth)acrylate, morpholinoethyl (meth)acrylate, dimethyl aminoethyl fumaratel, heterocyclic vinyl compounds [such as vinyl pyridines (e.g., 2-vinyl pyridine, 4-vinyl pyridine, Nvinyl pyridine), N-vinyl imidazoll; and 9. Quaternary ammonium salt group-containing monomers: N,N,Ntrialkyl-N-(meth)acryloyloxyalkylammonium salts [such as N,N,N-trimethyl-N-(meth)acryloyloxyethylammonium chloride, N,N,N-triethyl-N-(meth)acryloyloxyethylamonnium chloride, 2-hydroxy-3-(meth)-acryloyloxypropyl trimethyl ammonium chloride].

10. Ether-group containing monomers: methoxy polyethylene glycol (meth)acrylate; polyethylene glycol dimethacylate.

Desirable superabsorbent-forming monomers suitable for the process of the invention include without limitation aliphatic unsaturated monocarboxylic acids or salts thereof; specifically unsaturated monocarboxylic acids or salts thereof such as acrylic acid or salts thereof, methacrylic acid or salts thereof, or unsaturated dicarboxylic acids or salts thereof such as maleic acid or salts thereof, itaconic acid or salts thereof, which may be used alone or in combination.

Among these, acrylic acid or salts thereof and methacrylic acid or salts thereof are preferred, with especially preferred being acrylic acid or salts thereof.

Polymerizable monomers giving a water-absorbing polymer in the present invention are preferably aliphatic unsaturated carboxylic acids or salts thereof as described above, therefore, aqueous solutions of these polymerizable monomers are preferably aqueous solutions essentially containing an aliphatic unsaturated carboxylic acid or a salt thereof. As used here, the expression "essentially containing an aliphatic unsaturated carboxylic acid or a salt thereof" means that the aliphatic unsaturated carboxylic acid or a salt thereof is contained at 50 mol % or more, preferably 80 mol % or more on the basis of the total amount of the polymerizable monomer.

Suitable salts of aliphatic unsaturated carboxylic acids normally include water-soluble salts such as alkali metal salts, alkali earth metal salts, ammonium salts or the like. The neutrality is appropriately selected depending on the purpose, but 20–90 mol % of carboxyl group is preferably neutralized with an alkali metal salt or an ammonium salt in the case of acrylic acid. If the partial neutrality of an acrylic monomer is less than 20 mol %, the resulting water-absorbing polymer tends to have low water-absorbing capacity.

Acrylic monomers can be neutralized with alkali metal hydroxides or bicarbonates or ammonium hydroxide or the like, preferably alkali metal hydroxides such as sodium hydroxide and potassium hydroxide.

Superabsorbent-forming monomers may also include comonomers which are polymerizable along with any of the monomers listed above. The comonomers may form part of the same superabsorbent polymer precursor composition as the primary monomer, or may be part of a different superabsorbent polymer precursor composition, and may be added to the fibrous mixture using the same or different streams. While it may be desirable in some instances to add comonomers in different superabsorbent polymer precursor compositions, they may be added in the same precursor composition as the primary monomer if the primary monomer and comonomer will not spontaneously react with each other. Where the primary monomer is an aliphatic unsaturated carboxylic acid, suitable comonomers include without limitation secondary monomers such as (meth)acrylamide, (poly)ethylene glycol (meth)acrylate, 2-hydroxyethyl (meth)acrylate or even slightly water-soluble monomers including acrylate capped urethanes, acrylic alkyl esters such as methyl acrylate or ethyl acrylate may also be copolymerized in an amount within a range that does not affect performance of the resulting water-absorbing polymers in the present invention. As used herein, the term "(meth)acryl" means both "acryl" and "methacryl."

Aliphatic unsaturated carboxylic acids or salts thereof, especially acrylic acid or salts thereof sometimes form a self-crosslinked polymer by themselves, but may be positively induced to form a crosslinked structure using a crosslinker. The use of a crosslinker normally improves water-absorbing performance of the resulting water-absorbing polymer. Preferably, suitable crosslinkers include divinyl compounds copolymerizable with said polymerizable monomers such as N,N'-methylenebis(meth)acrylamide, (poly)ethylene glycol di(meth)acrylate and water-soluble compounds having two or more functional groups capable of reacting with a carboxylic acid including polyglycidyl ethers such as ethylene glycol diglycidyl ether, polyethylene grycol diglycidyl ether. Among them, N,N'-methylenebis (meth)acrylamide is especially preferred. Crosslinkers are used in an amount of 0.001–1% by weight, preferably 0.01–0.5% by weight on the basis of the amount of the monomer, and may be added in the same superabsorbent polymer precursor composition as the monomer, or as part of a different precursor composition.

The concentration of polymerizable monomers in an aqueous polymerizable monomer solution essentially containing an aliphatic unsaturated carboxylic acid or a salt thereof as described above is 20% or more, preferably 25% or more. Concentrations less than 20% by weight are not preferred because droplets having an appropriate viscosity are difficult to produce whereby the resulting water-absorbing polymer has insufficient water-absorbing capacity. The upper limit is preferably about 80% by weight in respect of handling of the polymerization reaction solution.

One or more polymerization initiators may be added in a different superabsorbent polymer precursor composition as the monomer(s). The polymerization initiator may be added as part of the same precursor composition as the monomer if subsequent activation is required or if the initiator is a single component of a redox pair. Alternatively, the polymerization initiators may be added as part of a different precursor composition as the monomer due to the fact that the polymerization initiators may act quickly to polymerize the monomer units once contact is made. When the monomer and polymerization initiator make initial contact in the fibrous web, the polymerization reaction is initiated, and occurs entirely within the fibrous web.

Polymerization initiators suitable for the present invention include without limitation somewhat water-soluble redox systems combining an oxidizing radical generator and a reducing agent. Such oxidizing agents include hydrogen peroxide, potassium bromate, N-bromosuccinimide, persulfates such as ammonium persulfate, sodium persulfate, or potassium persulfate, peroxides including hydroperoxides such as 1-butyl hydroperoxide or cumene hydroperoxide, secondary cerium salts, permanganates, chlorites, hypochlorites, etc., among which hydrogen peroxide is especially preferred. These oxidizing agents may be used in an amount of 0.001–10% by weight, desirably 0.01–2% by weight on the basis of polymerizable monomers.

Reducing agents are also used with the redox system, and may be added as part of the polymerization initiator. Suitable reducing agents are capable of forming a redox system with said oxidizing agents, specifically sulfites such as sodium sulfite or sodium hydrogensulfite, sodium thiosulfate, cobalt acetate, copper sulfate, ferrous sulfate, ferrous ammonium sulfate, sodium metabisulfite, tertiary amines or diamines, L-ascorbic acid or L-ascorbic acid alkali metal salts, etc. Among others, L-ascorbic acid or L-ascorbic acid alkali metal salts are especially preferred. These reducing agents are used in an amount of 0.001–10% by weight, preferably 0.01–2% by weight on the basis of polymerizable monomers. Desirably, the precursor composition containing the oxidizing radical generator is added using a different addition stream than is used for the reducing agents.

Process conditions, feed rates, and the like should be tailored to produce the desired composition for the absorbent nonwoven web composite. The process conditions and feed rates may be tailored to produce an absorbent nonwoven web composite having the following compositions:

| | Composition, % By Weight | | |
|---|---|---|---|
| | Hydrophilic Fibers | Superabsorbent Polymer Formed In Situ | Thermoplastic Fibers |
| Broad | 25–99 | 1–75 | 0–74 |
| Intermediate | 35–80 | 15–65 | 0–45 |
| Narrow | 40–70 | 20–50 | 10–30 |

Where a redox system of polymerization initiator(s) as described above is employed, the chemical reaction proceeds spontaneously. Otherwise, depending on the mechanism of chemical reaction employed, it may be necessary to raise the temperature of the fibrous web, irradiate it, or employ some other treatment in order to facilitate and optimize the chemical reaction.

In one embodiment of the invention, a first superabsorbent polymer precursor composition may contain all of the essential polymerization ingredients except for one initiator, which can be either an oxidizing agent or a reducing agent. The second superabsorbent polymer precursor composition may contain only that one initiator. When the first and second superabsorbent polymer precursor compositions come in contact with each other on or in the fibrous web, the chemical reaction proceeds spontaneously to form superabsorbent polymer.

In one embodiment of the invention, the first and second superabsorbent polymer precursor compositions are added to the fibrous webs at different times. For instance, the fibrous web may be initially treated with one of the superabsorbent polymer precursor compositions and then, in a separate stage, be treated with the other superabsorbent polymer precursor composition. By applying the first and second superabsorbent polymer precursor compositions in two different stages, there is virtual assurance that the two compositions will not contact each other or chemically react before both are present on or in the fibrous web. Of course, the first and second superabsorbent polymer precursor compositions can be applied in a single stage (at the same time) provided that care is taken to avoid commencement of the chemical reaction before both precursor compositions contact the fibrous web.

In one embodiment of the invention, the first and second superabsorbent polymer precursor compositions are combined on or in the fibrous web, and are chemically reacted to form a superabsorbent polymer. Then, to further advance and complete the chemical reaction, a third superabsorbent polymer precursor composition (for instance, one containing a second polymerization initiator or a second quantity of an original polymerization initiator) is added to the fibrous web.

Examples of superabsorbent polymers which may be formed in situ include without limitation the alkali metal and ammonium salts of poly(acrylic acid) and poly(methacrylic acid), poly(acrylamides), poly(vinyl ethers), maleic anhydride copolymers with vinyl ethers and alpha-olefins, poly(vinyl pyrrolidone), poly(vinylmorpholinone), and mixtures and copolymers thereof. Further superabsorbent materials (some of which may be formed before addition to the fibrous web) include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic superabsorbent polymers can also be useful in the present invention. Other suitable absorbent gelling materials are disclosed by Assarsson et al. in U.S. Pat. No. 3,901,236 issued Aug. 26, 1975. Known processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Superabsorbent materials may be xerogels which form hydrogels when wetted. The term "hydrogel," however, has commonly been used to also refer to both the wetted and unwetted forms of the superabsorbent polymer material. The superabsorbent materials can be in many forms such as flakes, powders, particulates, fibers, continuous fibers, networks, solution spun filaments and webs. The particles can be of any desired shape, for example, spiral or semi-spiral, cubic, rod-like, polyhedral, etc. Needles, flakes, fibers, and combinations may also be used.

Pre-formed superabsorbents are generally available in particle sizes ranging from about 20 to about 1000 microns. Examples of suitable commercially available particulate superabsorbents include HYSORB® P7050 and HYSORB® P7060, available from BASF Corporation, DRYTECH® 2035LD available from Dow Chemical Co. located in Midland, Mich., and FAVOR® SXM 880, available from Stockhausen located in Greensboro, N.C. An example of a fibrous superabsorbent is OASIS® 101, available from Technical Absorbents, located in Grimsby, United Kingdom.

The resulting absorbent composite material includes a plurality of hydrophilic fibers having superabsorbent particles formed in situ which stick to the surfaces of the fibers, and which are not freely movable. Suitably, the superabsorbent particles are formed in situ in such quantity which permits them to be spaced apart from each other by an average distance of about 50–4000 microns, desirably about 200–3000 microns, so that the superabsorbent particles may swell in the presence of liquid without contacting each other. Suitably, the in situ formed superabsorbent particles have the same average diameter in the dry, unswollen state as conventional, pre-formed superabsorbent particles. The average dry particle diameter may range from about 10–1000 microns, desirably about 20–500 microns. A primary advantage of the absorbent composite materials of the invention is that the superabsorbent particles stick to the fibrous substrate, so that the distance between the superabsorbent particles is maintained.

The absorbent composite material of the invention is useful in a wide variety of absorbent articles, particularly as an absorbent core material in personal care absorbent articles and medical absorbent articles. Personal care absorbent articles include diapers, training pants, swim wear, absorbent underpants, baby wipes, adult incontinence products, feminine hygiene products and the like. Medical absorbent articles include medical absorbent garments, drapes, gowns, bandages, wound dressings, underpads, wipes, and the like.

While the embodiments of the invention described herein are presently preferred, various modifications and improvements can be made without departing from the spirit and scope of the invention. The scope of the invention is indicated in the appended claims, and all changes that fall within the meaning and range of equivalents are intended to be embraced therein.

We claim:

1. A process for making an absorbent fibrous web composite, comprising the steps of:
    providing a first superabsorbent polymer precursor composition;
    providing a second superabsorbent polymer precursor composition capable of chemically reacting with the first superabsorbent polymer precursor composition upon contact;
    providing a pre-formed fibrous web including a plurality of hydrophilic fibers;
    applying the first superabsorbent polymer precursor composition as spaced apart microdroplets having a diameter of about 10 to about 1000 microns to the fibrous web using a non-contact printing process which is not a spraying process;
    separately applying the second superabsorbent polymer precursor composition as spaced apart microdroplets having a diameter of about 10 to about 1000 microns to the fibrous web using a non-contact printing process which is not a spraying process, whereupon the second superabsorbent polymer precursor composition initially comes into contact with the first superabsorbent polymer precursor composition after being applied to the fibrous web; and
    chemically reacting the first and second superabsorbent polymer precursor compositions on or in the fibrous web to form superabsorbent polymer consisting essentially of spaced apart particles having a spacing, of 50–4000 microns and a dry diameter of about 10 to about 1000 microns;
    wherein the superabsorbent polymer constitutes 20–75% by weight of the absorbent composite.

2. The process of claim 1, wherein the microdroplets of the first and second precursor compositions have diameters of about 50–500 microns.

3. The process of claim 1, wherein the microdroplets of the first and second precursor compositions have viscosities of about 5–1000 centipoise.

4. The process of claim 1, wherein the microdroplets of the first and second precursor compositions have viscosities of about 10–500 centipoise.

5. The process of claim 1, wherein the microdroplets of the first and second precursor compositions have viscosities of about 20–100 centipoise.

6. The process of claim 1, wherein the first and second superabsorbent polymer precursor compositions are separately applied in two different stages.

7. The process of claim 1, wherein the first and second superabsorbent polymer precursor compositions are separately applied in a single stages.

8. The process of claim 1, wherein the first superabsorbent polymer precursor composition comprises a monomer and the second superabsorbent polymer precursor composition comprises a polymerization initiator.

9. The process of claim 1, wherein the first and second superabsorbent polymer precursor compositions chemically react spontaneously upon contact with each other.

10. The process of claim 1, wherein the nonwoven web further comprises a plurality of thermoplastic fibers.

11. The process of claim 1, wherein the hydrophilic fibers comprise cellulose fibers.

12. The process of claim 1, wherein the hydrophilic fibers comprise absorbent fibers.

13. The process of claim 1, wherein the hydrophilic fibers comprise staple fibers.

14. A process for making an absorbent fibrous web composite, comprising the steps of:
    providing a first superabsorbent polymer precursor composition including a monomer;
    providing a second superabsorbent polymer precursor composition including a polymerization initiator;
    providing a pre-formed fibrous web including a plurality of fibers;
    applying the first superabsorbent polymer precursor composition as spaced apart microdroplets having a diameter of about 10 to about 1000 microns to the fibrous web using a non-contact printing process which is not a spraying process;
    separately applying the second superabsorbent polymer precursor composition as spaced apart microdroplets having a diameter of about 10 to about 1000 microns to the fibrous web using a non-contact printing process which is not a spraying process, whereupon the second superabsorbent polymer precursor composition initially comes into contact with the first superabsorbent polymer precursor composition after being applied to the fibrous web; and
    chemically reacting the first and second superabsorbent polymer precursor compositions on or in the fibrous web to form superabsorbent polymer consisting essentially of spaced apart particles having a spacing of 50–4000 microns and a dry diameter of about 10 to about 1000 microns;
    wherein the superabsorbent polymer constitutes 20–75% by weight of the absorbent composite.

15. The process of claim 14, wherein the first and second superabsorbent polymer precursor compositions are separately applied in two different stages.

16. The process of claim 14, wherein the first and second superabsorbent polymer precursor compositions are separately applied in a single stage.

17. The process of claim 14, wherein the monomer comprises a compound selected from the group consisting of aliphatic unsaturated monocarboxylic acids and their salts, methacrylic acids and their salts, unsaturated dicarboxylic acids and their salts, and combinations thereof.

18. The process of claim 14, wherein the monomer comprises a compound selected from the group consisting of acrylic acid and its salts, methacrylic acid and its salts, and combinations thereof.

19. The process of claim 14, wherein the polymerization initiator comprises a redox system.

20. The process of claim 19, wherein the redox system comprises a water-soluble redox system.

21. The process of claim 19, wherein the redox system comprises an oxidizing radical generator and a reducing agent.

22. The process of claim 19, wherein the oxidizing agent comprises a compound selected from peroxides, persulfates, permanganates, chlorites, hypochlorites, and combinations thereof.

23. The process of claim 19, wherein the reducing agent comprises a compound selected from sulfites, ascorbic acid, alkaline metal salts, and combinations thereof.

24. A process for making an absorbent nonwoven web composite, comprising the steps of:

provMENTOing a pre-formed nonwoven web including about 25–100% by weight absorbent fibers and about 0–75% by weight thermoplastic fibers;

providing a first superabsorbent polymer precursor composition;

providing a second superabsorbent polymer precursor composition capable of chemically reacting with the first superabsorbent polymer precursor composition upon contact;

applying the first superabsorbent polymer precursor composition to the nonwoven web as spaced apart microdroplets having a diameter of about 10 to about 1000 microns using a non-contact printing process which is not a spraying process;

separately applying the second superabsorbent polymer precursor composition to the nonwoven web as spaced apart microdroplets having a diameter of about 10 to about 1000 microns using a non-contact printing process which is not a spraying process, whereupon the second superabsorbent polymer precursor composition initially comes into contact with the first superabsorbent polymer precursor composition after being applied to the nonwoven web; and chemically reacting the first and second superabsorbent polymer precursor compositions on or in the nonwoven web to form superabsorbent polymer consisting essentially of spaced apart particles having a spacing of 50–4000 microns and a dry diameter of about 10 to about 1000 microns;

wherein the superabsorbent polymer constitutes 20–75% by weight of the composite.

25. The process of claim 24, wherein the microdroplets have diameters of about 50–500 microns.

26. The process of claim 24, wherein the pre-formed nonwoven web comprises about 50–100% by weight absorbent fibers and about 0–50% by weight thermoplastic fibers.

27. The process of claim 24, wherein the pre-formed nonwoven web comprises about 60–90% by weight absorbent fibers and about 10–40% by weight thermoplastic fibers.

* * * * *

UNITED STATES PATENT AND TRADEMARK OFFICE
CERTIFICATE OF CORRECTION

PATENT NO. : 6,918,981 B2
DATED : July 19, 2005
INVENTOR(S) : Young C. Ko et al.

It is certified that error appears in the above-identified patent and that said Letters Patent is hereby corrected as shown below:

Column 12,
Line 9, "single stages" should read -- single stage --.

Signed and Sealed this

Twentieth Day of September, 2005

JON W. DUDAS
*Director of the United States Patent and Trademark Office*